(12) United States Patent
Sagar et al.

(10) Patent No.: US 7,554,549 B2
(45) Date of Patent: Jun. 30, 2009

(54) SYSTEM AND METHOD FOR TRACKING FACIAL MUSCLE AND EYE MOTION FOR COMPUTER GRAPHICS ANIMATION

(75) Inventors: Mark Sagar, Venice, CA (US); Remington Scott, Santa Monica, CA (US)

(73) Assignees: Sony Corporation, Tokyo (JP); Sony Pictures Entertainment Inc., Culver City, CA (US)

( * ) Notice: Subject to any disclaimer, the term of this patent is extended or adjusted under 35 U.S.C. 154(b) by 53 days.

(21) Appl. No.: 10/984,488

(22) Filed: Nov. 8, 2004

(65) Prior Publication Data

US 2006/0071934 A1    Apr. 6, 2006

Related U.S. Application Data

(60) Provisional application No. 60/616,049, filed on Oct. 4, 2004, provisional application No. 60/615,268, filed on Oct. 1, 2004.

(51) Int. Cl.
*G06T 13/00* (2006.01)
*G06T 15/70* (2006.01)
*A61B 5/04* (2006.01)

(52) U.S. Cl. .................... 345/473; 345/474; 600/546

(58) Field of Classification Search ............... 600/546; 345/473–474
See application file for complete search history.

(56) References Cited

U.S. PATENT DOCUMENTS

| 4,320,768 | A | * | 3/1982 | Ledley et al. ............... 600/546 |
| 4,690,142 | A | * | 9/1987 | Ross et al. ................... 607/62 |
| 4,836,219 | A | * | 6/1989 | Hobson et al. .............. 600/595 |
| 5,517,021 | A | * | 5/1996 | Kaufman et al. ............ 250/221 |
| 5,694,939 | A | * | 12/1997 | Cowings ..................... 600/484 |
| 6,026,321 | A | | 2/2000 | Miyata et al. |
| 6,032,072 | A | * | 2/2000 | Greenwald et al. .......... 600/544 |
| 6,079,829 | A | * | 6/2000 | Bullwinkel ................. 351/210 |
| 6,249,292 | B1 | * | 6/2001 | Christian et al. ............ 345/473 |
| 6,324,296 | B1 | | 11/2001 | McScherry et al. |
| 6,379,393 | B1 | * | 4/2002 | Mavroidis et al. .......... 623/25 |
| 6,673,027 | B2 | * | 1/2004 | Fischer ....................... 600/595 |

(Continued)

OTHER PUBLICATIONS

Lucero, Jorge C., Munhall, Kevin G. "A Model of Facial Biomechanics for Speech Production," Nov. 1999, Acoustical Society of America, vol. 106, No. 5, pp. 2834-2842.*

(Continued)

*Primary Examiner*—Kee M Tung
*Assistant Examiner*—Crystal Murdoch
(74) *Attorney, Agent, or Firm*—O'Melveny & Myers LLP

(57) ABSTRACT

A motion tracking system enables faithful capture of subtle facial and eye motion using a surface electromyography (EMG) detection method to detect muscle movements and an electrooculogram (EOG) detection method to detect eye movements. An embodiment of the motion tracking animation system comprises a plurality of pairs of EOG electrodes adapted to be affixed to the skin surface of the performer at locations adjacent to the performer's eyes. The EOG data comprises electrical signals corresponding to eye movements of a performer during a performance. Programming instructions further provide processing of the EOG data and mapping of processed EOG data onto an animated character. As a result, the animated character will exhibit he same muscle and eye movements as the performer.

11 Claims, 7 Drawing Sheets

U.S. PATENT DOCUMENTS

| | | |
|---|---|---|
| 6,720,984 B1 * | 4/2004 | Jorgensen et al. .......... 715/863 |
| 6,774,885 B1 * | 8/2004 | Even-Zohar ................ 345/156 |
| 6,788,333 B1 | 9/2004 | Uyttendaele et al. |
| 7,012,634 B2 | 3/2006 | Vogel et al. |
| 7,012,637 B1 | 3/2006 | Blume et al. |
| 7,068,277 B2 * | 6/2006 | Menache ................... 345/473 |
| 7,106,358 B2 | 9/2006 | Valliath et al. |
| 2002/0188216 A1 * | 12/2002 | Kayyali et al. .............. 600/544 |
| 2003/0160791 A1 * | 8/2003 | Breton et al. ............... 345/473 |
| 2003/0215130 A1 | 11/2003 | Nakamura |
| 2004/0095352 A1 * | 5/2004 | Huang ....................... 345/473 |
| 2004/0155962 A1 | 8/2004 | Marks |
| 2004/0166954 A1 | 8/2004 | Erickson |
| 2004/0179013 A1 * | 9/2004 | Menache ................... 345/473 |
| 2005/0261559 A1 * | 11/2005 | Mumford et al. ........... 600/300 |
| 2006/0004296 A1 * | 1/2006 | Huiku et al. ................ 600/513 |
| 2007/0299484 A1 * | 12/2007 | Greenberg et al. ........... 607/54 |
| 2008/0021516 A1 * | 1/2008 | Greenberg et al. ........... 607/54 |

OTHER PUBLICATIONS

Lee, Sooha Park; "Facial Animation System with Realistic Eye Movement Based on a Cognitive Model for Virtual Agents;" 2002; Dissertation in Computer and Information Science; University of Pennsylvania; pp. 1-4, 21 and 51-53.*

Lapatki, B. G. et al.; A surface EMG electrode for the simultaneous observation of multiple facial muscles; Mar. 15, 2003; Journal of Neuroscience Methods; vol. 123, No. 2; pp. 117-128.*

Joyce, C. A. et al.; "Tracking eye fixations with electroocular and electroencephalographic recordings;" 2002, Psychophysiology; Cambridge University Press; vol. 39; pp. 607-618.*

Malmivuo, J. et al.; "Bioelectromagnetism, Principles and Applications of Bioelectric and Biomagnetic Fields;" 1995, Oxford University Press; Chapter 28, pp. 538-549.*

\* cited by examiner

SYSTEM AND METHOD FOR TRACKING FACIAL MUSCLE AND EYE MOTION FOR COMPUTER GRAPHICS ANIMATION

RELATED APPLICATION DATA

This patent application claims priority pursuant to 35 U.S.C. § 119(c) to the following provisional patent applications: (a) Ser. No. 60/616,049, filed Oct. 4, 2004 for SYSTEM AND METHOD FOR CAPTURING FACIAL AND EYE MOTION; and (b) Ser. No. 60/615,268, filed Oct. 1, 2004 for TRACKING OF FACIAL FEATURE MOVEMENTS WITHOUT VISUAL FACE CAPTURE.

BACKGROUND OF THE INVENTION

1. Field of the Invention

The present invention relates to three-dimensional graphics and animation, and more particularly, to a motion tracking system that enables capture of facial and eye motion of a performer without the use of cameras for use in producing a computer graphics animation.

2. Description of Related Art

Motion capture systems are used to capture the movement of a real object and map it onto a computer generated object. Such systems are often used in the production of motion pictures and video games for creating a digital representation of a person that is used as source data to create a computer graphics (CG) animation. In a typical system, a performer wears a suit having markers attached at various locations (e.g., having small reflective markers attached to the body and limbs) and digital cameras record the movement of the performer from different angles while illuminating the markers. The system then analyzes the images to determine the locations (e.g., as spatial coordinates) and orientation of the markers on the performer's suit in each frame. By tracking the locations of the markers, the system creates a spatial representation of the markers over time and builds a digital representation of the performer in motion. The motion is then applied to a digital model, which may then be textured and rendered to produce a complete CG representation of the actor and/or performance. This technique has been used by special effects companies to produce incredibly realistic animations in many popular movies.

Motion capture systems are also used to track the motion of facial features of an actor to create a representation of the actor's facial motion and expression (e.g., laughing, crying, smiling, etc.). As with body motion capture, markers are attached to the actor's face and cameras record the actor's expressions. Since facial movement involves relatively small muscles in comparison to the larger muscles involved in body movement, the facial markers are typically much smaller than the corresponding body markers, and the cameras typically have higher resolution than cameras usually used for body motion capture. The cameras are typically aligned in a common plane with physical movement of the actor restricted to keep the cameras focused on the actor's face. The facial motion capture system may be incorporated into a helmet or other implement that is physically attached to the actor so as to uniformly illuminate the facial markers and minimize the degree of relative movement between the camera and face.

An advantage of motion capture systems over traditional animation techniques, such as keyframing, is the capability of real-time visualization. The production team can review the spatial representation of the performer's motion in real-time or near real-time, enabling the actor to alter the physical performance in order to capture optimal data. Moreover, motion capture systems detect subtle nuances of physical movement that cannot be easily reproduced using other animation techniques, thereby yielding data that more accurately reflects natural movement. As a result, animation created using source material that was collected using a motion capture system will exhibit a more lifelike appearance.

Notwithstanding these advantages of motion capture systems, a drawback of conventional motion capture systems is that they cannot capture eye motion. Since the markers cannot be affixed to the performer's eyes, the eye movement is not detected by the motion capture cameras. This eye movement must then be added during the subsequent CG animation process. In addition to making the animation process more cumbersome, the resulting animation product is less realistic since it may not include subtle eye movement that occurs during a performance.

Another drawback of conventional motion capture systems that rely upon cameras is that motion data of a performer may be occluded by interference with other objects, such as props or other actors. Specifically, if a portion of the body or facial markers is blocked from the field of view of the digital cameras, then data concerning that body or facial portion is not collected. This results in an occlusion or hole in the motion data. While the occlusion can be filled in later during post-production using conventional computer graphics techniques, the fill data lacks the quality of the actual motion data, resulting in a defect of the animation that may be discernable to the viewing audience. To avoid this problem, conventional motion capture systems limit the number of objects that can be captured at one time, e.g., to a single performer. This also tends to make the motion data appear less realistic, since the quality of a performer's performance often depends upon interaction with other actors and objects. Moreover, it is difficult to combine these separate performances together in a manner that appears natural.

Outside of the entertainment industry, there are many other circumstances in which it would be desirable to capture or track facial muscle and/or eye movement without reliance upon optical cameras. For example, automatic speech recognition devices, access control systems, electronic storage and retrieval systems for personal profiles and medical/dental screening systems could make use of such analysis techniques. Speech recognition systems that utilize analyses of facial features may find wide application in noisy environments where it is difficult to utilize acoustic speech recognition alone, e.g., in a military aircraft or in a factory. Each of these potential applications presently lack an effective means for accurately translating an individual's facial features into useful electronic data. This is particularly problematic where the individual is continually changing facial orientation with respect to the detection equipment.

Accordingly, it would be desirable to provide a motion tracking system that overcomes these and other drawbacks of the prior art. More specifically, it would be desirable to provide a motion tracking system that enables faithful capture of subtle facial and eye motion of a performer without the use of cameras.

SUMMARY OF THE INVENTION

The present invention overcomes the drawbacks of the prior art by providing a motion tracking system that enables faithful capture of subtle facial and eye motion. The invention uses a surface electromyography (EMG) detection method to detect muscle movements, and an electrooculogram (EOG) detection method to detect eye movements. Signals corresponding to the detected muscle and eye movements are used to control an animated character to exhibit the same movements performed by a performer.

More particularly, an embodiment of the motion tracking animation system comprises a plurality of pairs of electromyography (EMG) electrodes adapted to be affixed to a skin surface of a performer at plural locations corresponding to respective muscles, and a processor operatively coupled to the plurality of pairs of EMG electrodes. The processor includes programming instructions to perform the functions of acquiring EMG data from the plurality of pairs of EMG electrodes. The EMG data comprises electrical signals corresponding to muscle movements of the performer during a performance. The programming instruction further include processing the EMG data to provide a digital model of the muscle movements, and mapping the digital model onto an animated character. As a result, the animated character will exhibit the same muscle movements as the performer.

In an embodiment of the invention, a plurality of pairs of electrooculogram (EOG) electrodes are adapted to be affixed to the skin surface of the performer at locations adjacent to the performer's eyes. The processor is operatively coupled to the plurality of pairs of EOG electrodes and further includes programming instructions to perform the functions of acquiring EOG data from the plurality of pairs of EOG electrodes. The EOG data comprises electrical signals corresponding to eye movements of the performer during a performance. The programming instructions further provide processing of the EOG data and mapping of the processed EOG data onto the animated character. This permits the animated character to exhibit the same eye movements as the performer.

A more complete understanding of the motion tracking system that enables capture of facial and eye motion of a performer for use in producing a computer graphics animation will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

As will be further described below, the present invention satisfies the need for a motion tracking system that enables faithful capture of subtle facial and eye motion of a performer without the use of cameras. In the detailed description that follows, like element numerals are used to describe like elements illustrated in one or more of the drawings.

Figure 1:
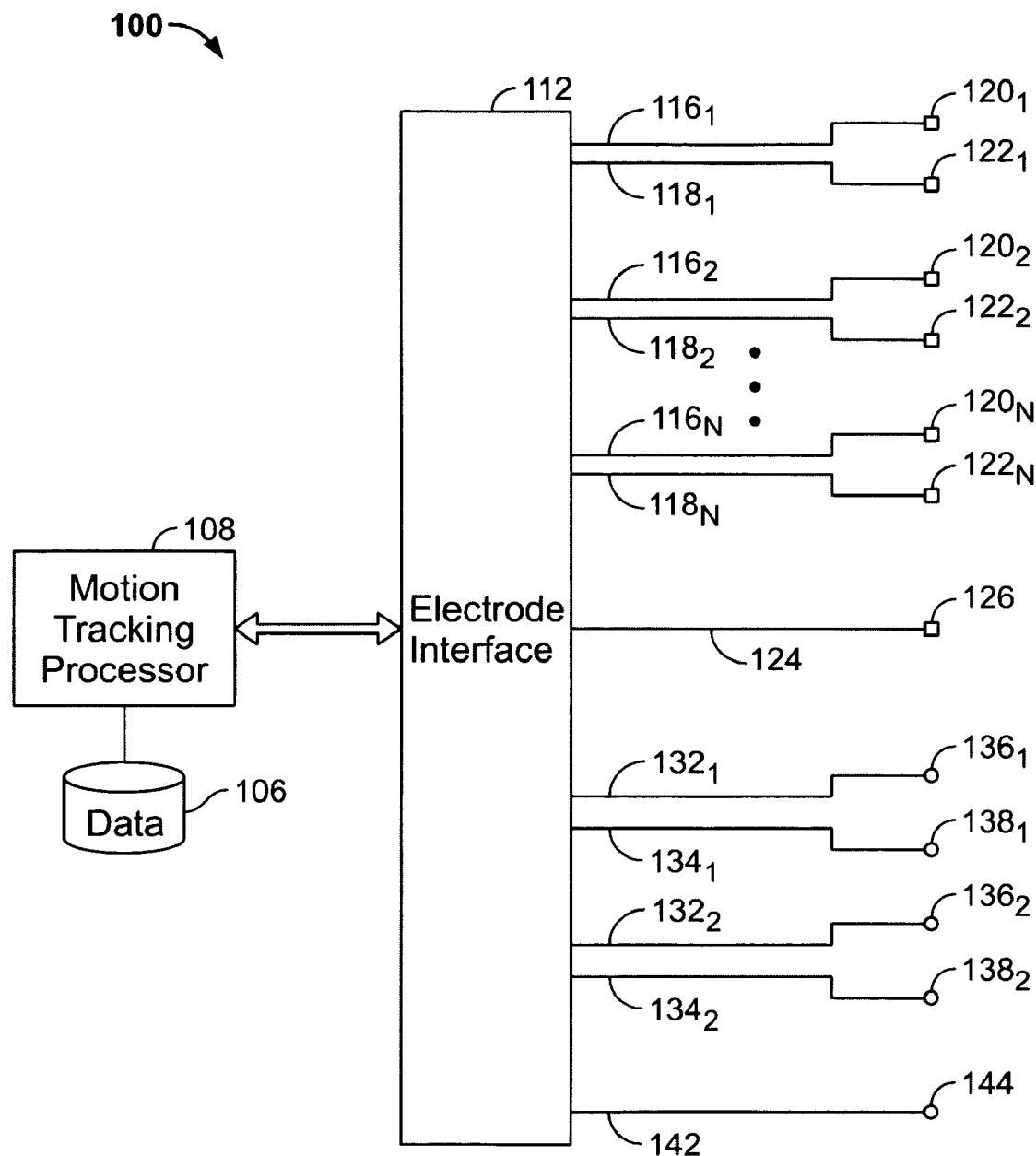
FIG. 1 is a block diagram illustrating a motion tracking system in accordance with an embodiment of the present invention.

Referring first to FIG. 1, a block diagram illustrates a motion tracking system 100 in accordance with an embodiment of the present invention. The motion tracking system 100 includes a motion tracking processor 108 adapted to communicate with a plurality of facial muscular electrode pairs and a plurality of eye motion electrode pairs through a suitable electrode interface 112. The motion tracking processor 108 may further comprise a programmable computer having a data storage device 106 adapted to enable the storage of associated data files. As known in the art, one or more computer workstations may be coupled to the motion tracking processor 108 using a network to enable multiple graphic artists to work with the stored data files in the process of creating a computer graphics animation. The motion tracking processor 108 may further include a computer graphics animation system such as provided by a commercial software package that enables the creation of 3D graphics and animation for the entertainment industry, such as the Maya® software product line sold by Alias|Wavefront™ or other like products. It should be understood that the computer graphics animation system may comprise an entirely separate computer hardware and software system from the motion tracking processor 108, or alternatively, may be incorporated with the motion tracking processor 108 (e.g., as a "plug-in") as part of a common hardware and software system.

The muscular electrode pairs include electrodes $120_1, 122_1$ through $120_N, 122_N$, which are coupled to the electrode interface 112 through respective electrical conductors $116_1, 118_1$ through $116_N, 118_N$. Also, a ground electrode 126 is coupled to the electrode interface 112 through electrical conductor 124. In a preferred embodiment of the invention, the muscular electrode pairs comprise surface electromyography (EMG) electrodes that measure a voltage difference caused by a depolarization wave that travels along the surface of a muscle that occurs when the muscle flexes. The signals detected by the surface electrodes are typically in the range of 5 mV. The electrodes should be aligned with expected direction of an electrical impulse (or aligned perpendicular to impulses that should be excluded).

The eye motion electrode pairs include electrodes $136_1, 138_1$ and $136_2, 138_2$, which are coupled to the electrode interface 112 through respective electrical conductors $132_1, 134_1$ and $132_2, 134_2$. Also, a ground electrode 144 is coupled to the electrode interface 112 through electrical conductor 142. In a preferred embodiment, eye motion is detected by acquiring and measuring electro-oculogram (EOG) from the eyes.

Figure 2:
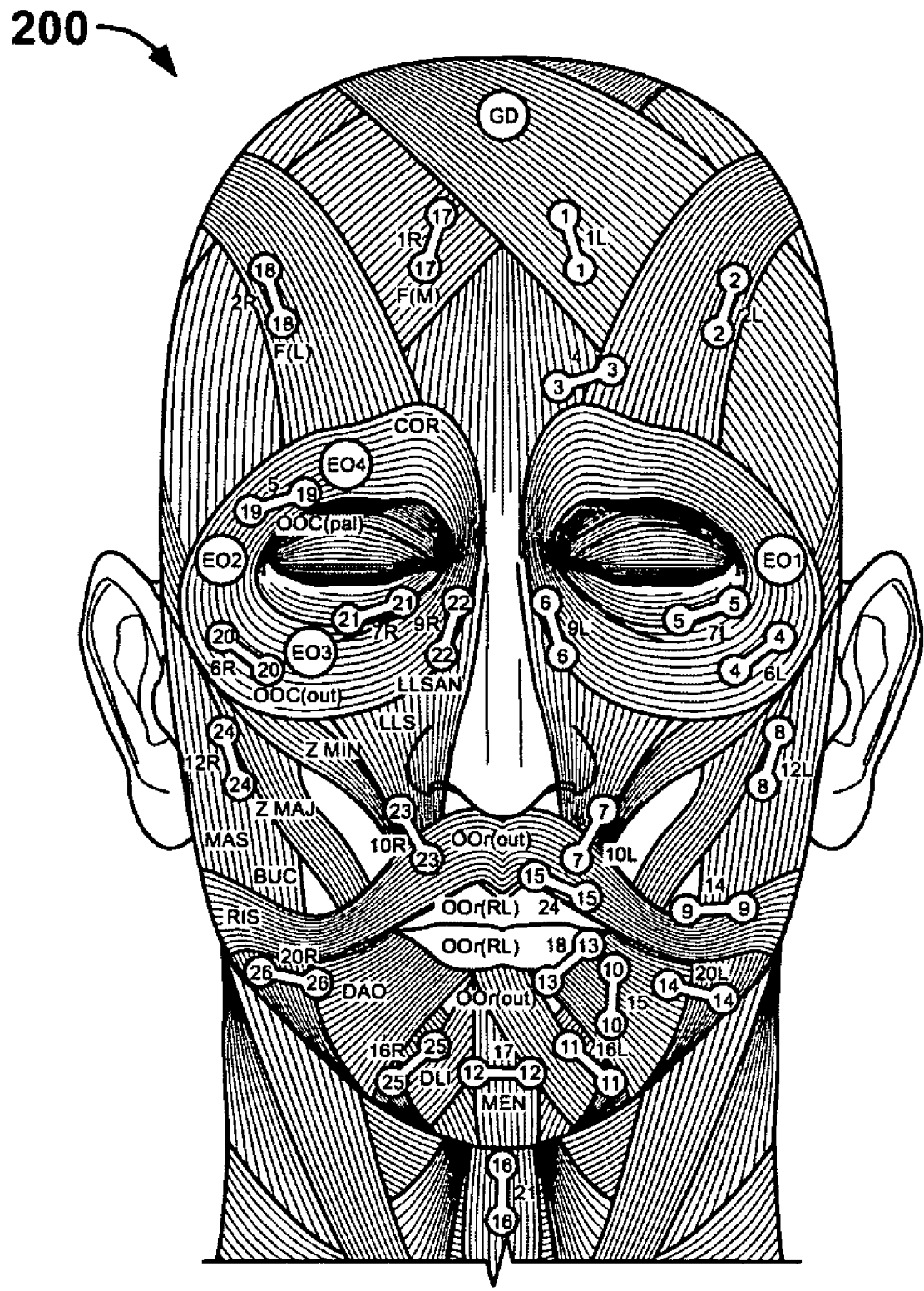
FIG. 2 is a front view of a human facial muscular structure including exemplary electrode placement locations.

FIG. 2 illustrates a human anatomical model 200 showing a facial muscular system having exemplary designated facial muscle locations for the EMG electrode pairs. A pair of EMG electrodes is used to capture data from each respective muscle group. For example, electrode pair location 1L corresponds to muscles responsible for raising the left inner brow, electrode pair location 2L corresponds to muscles responsible for raising the left outer brow, electrode pair location 3 corresponds to muscles responsible for lowering the brow, etc. The electrode pairs are affixed to the skin surface of the performer at the designated locations by conventional manner, such as using a cosmetic glue. It should be appreciated that movement of the corresponding muscles by a performer will produce associated electrical signals that are detected by the corresponding electrodes. Since the muscles of every person are slightly different, it may require a certain amount of experimentation accurately locate and position the electrodes for each performer to achieve optimum data collection.

As known in the medical art, the upper facial muscles are responsible for changing the appearance of the eyebrows, forehead, and upper and lower eyelids. The Frontalis muscles in the upper portion of the face contract isotonically towards static insertion points on the cranium, enabling the surface tissue (i.e., skin) to bunch and wrinkle perpendicularly to the direction of the muscle. The lower facial muscles are made up of several distinct groups, including the Zygomaticus major muscles that contract in an angular direction from the lips toward the cheekbones, the Orbicularis Oculi muscles that are circular or elliptical in nature and extend around the eyes, the Obicularis Oris muscles that extend around the mouth, the Buccinator muscles that contract horizontally toward the ears, and others controlling various miscellaneous actions. The muscles of the mouth have particularly complex muscular interaction. The Obicularis Oris is a sphincter muscle with no attachment to bone. Three primary muscles, i.e., M. Levator, Labii Superioris and Alaeque Nasi, join from above, while the M. Buccinator joins at the major node of the mouth and contracts horizontally. The M. Depressor, Anguli Oris, M. Depressor Labii Inferioris and Mentalis each contract obliquely and vertically. Facial expressions are formed by complex and combined movements of these upper and lower facial muscles.

FIG. 2 also shows exemplary designated locations for the EOG electrode pairs. Electrode pair locations EO1 and EO2 adjacent to the eyes are suitable to detecting signals associated with left/right movement of the eyes. Electrode pair locations EO3 and EO4 below and above one of the eyes are suitable to detecting signals associated with up/down movement of the eyes. A ground electrode location GD is positioned on the forehead. It is noted that the ground electrode could be affixed anywhere on the body where it will not interfere with the application and action of the facial muscles, such as the neck, shoulder, elbow, etc. The forehead represents a convenient location for the ground electrode since it is close in proximity to the other electrodes without interference with facial muscle action. It is noted that a second ground electrode may be necessary for the EMG electrodes, and this second ground electrode may be positioned in the same region as the EOG ground electrode. Since the dipoles representing the performer's two eyes will move in parallel, it is only necessary to collect up/down motion from one of the eyes. As with the EMG electrodes, the EOG electrodes are affixed to the skin surface of the performer at the designated locations by conventional manner, such as using a cosmetic glue.

Figure 6:
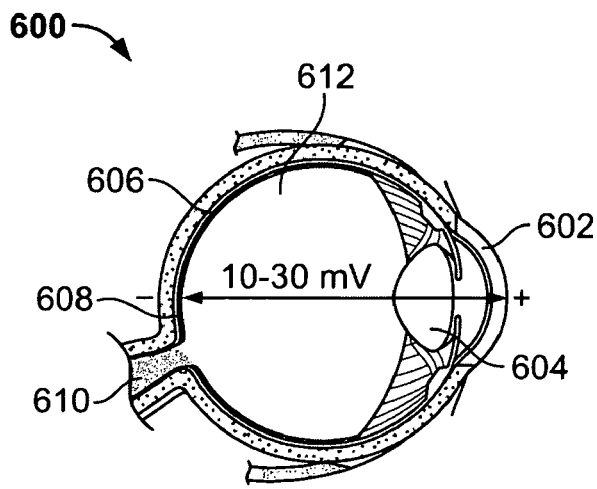
FIG. 6 is a side sectional view of a human eye showing the voltage potential that exists between cornea and the ocular fundus.

Referring briefly to FIG. 6, a side sectional view of a human eye 600 is shown. The cornea 602 is located at the front surface of the eye, and provides a surface that transmits light rays reflected from an object. The light rays are bent, refracted and focused by the cornea 602, lens 604, and vitreous 612. The ocular fundus 608 provides the concave interior of the eye, which includes the retina 606. The lens 602 focuses an image of the object onto the retina 606, which converts the light rays into electrical impulses that are transmitted to the brain through the optic nerve 610. As understood in the art, a voltage potential exists between the cornea 602 and the ocular fundus 608. This voltage potential comprises a dipole that emits a measurable electric field such that the variations of the electric field is related to the movement of the eyes.

Figure 7A:
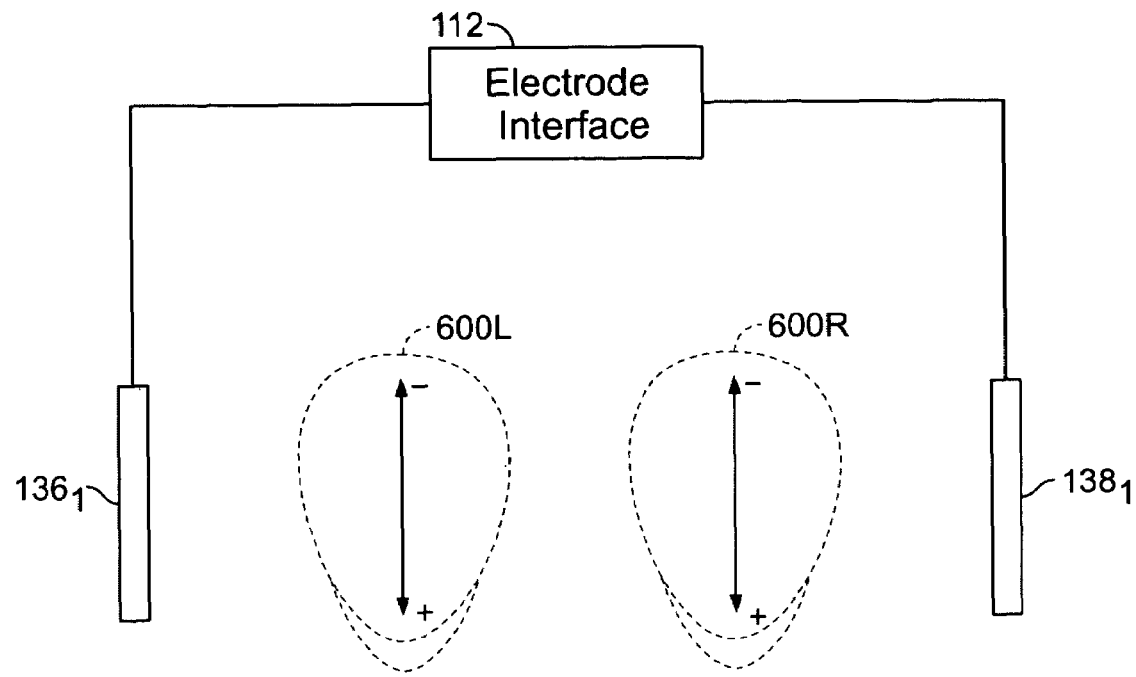
FIGS. 7A and 7B are schematic drawings showing the electrical field measurement corresponding to eye movement.
Figure 7B:
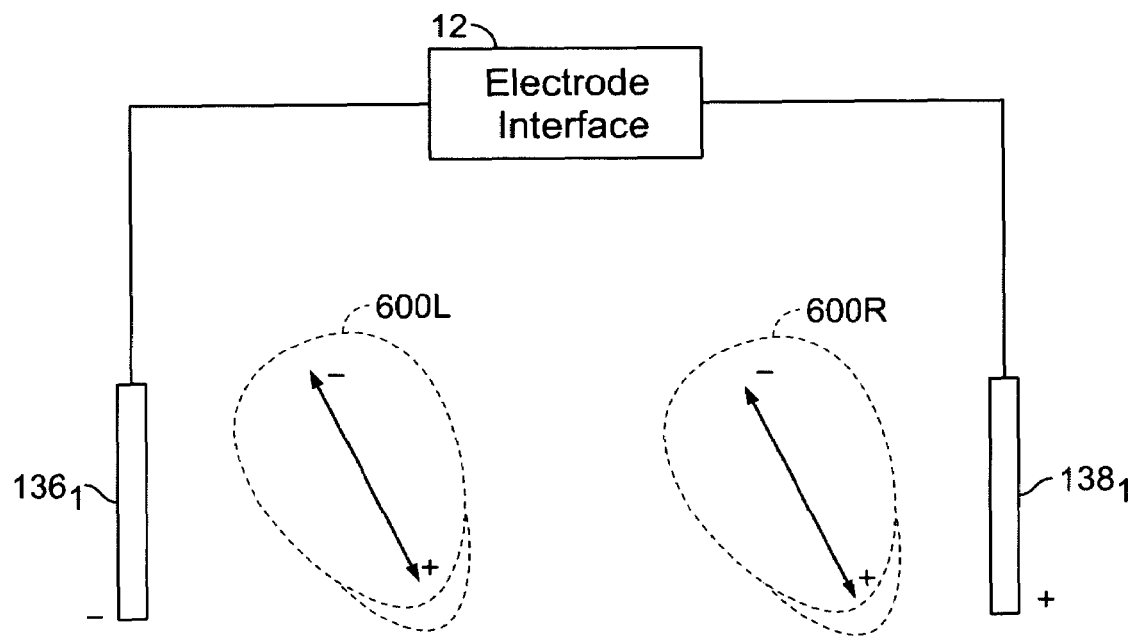

FIGS. 7A and 7B illustrate two dipoles surrounded by an electrode pair $136_1$, $138_1$. The two dipoles correspond to each of a performer's eyes 600L, 600R. As shown in FIG. 7A, the electric field measured between the electrodes $136_1$, $138_1$ is null when the dipoles (i.e., eyes) are facing in a forward direction. In FIG. 7B, the dipoles are oriented to the right, thereby inducing a positive electric field between the electrodes $136_1$, $138_1$. The electric field variation between the electrodes $136_1$, $138_1$ relative to ground provides suitable positional information for the eyes. This electrical field variation remains fairly linear with respect to eye movement for a range of roughly ±20° from the nominal forward direction.

Returning now to FIG. 1, the motion tracking processor 108 provides signal processing and amplification of the signals detected by the EMG and EOG electrodes. With regard to the EMG electrodes, the signal processing may include rectification of the received signals. Because the raw signal is biphasic, its mean value is zero. Rectification allows current flow in only one direction, and so "flips" the signal's negative content across the zero axis, making the whole signal positive. The phase component of the signals received from the EOG electrodes is critical to determining the direction of the eyes, and so no rectification of these signals would not be performed. The signal processing may also include filtering and linear envelope detection of the received signals. The EMG signal is actually a composite of many signals, as well as some noise. These voltages also rise and fall at various rates or frequencies, forming a frequency spectrum. The motion tracking processor 108 may filter the composite signal and eliminate unwanted and meaningless electrical noise such as movement artifact. Most EMG exists in a frequency range between 20 and 200 Hz. Movement artifacts have frequencies less than 10 Hz, and noise has a frequency range above the desired EMG range. Accordingly, the movement artifacts and noise can be removed by passing the signal through a band-pass filter. The electrode interface 112 and/or motion tracking processor 108 may also amplify the received signals to raise them to a level suitable for signal processing. In an embodiment of the invention, the electrode interface may be provided by the Myopac system made by Run Technologies.

Figure 3:
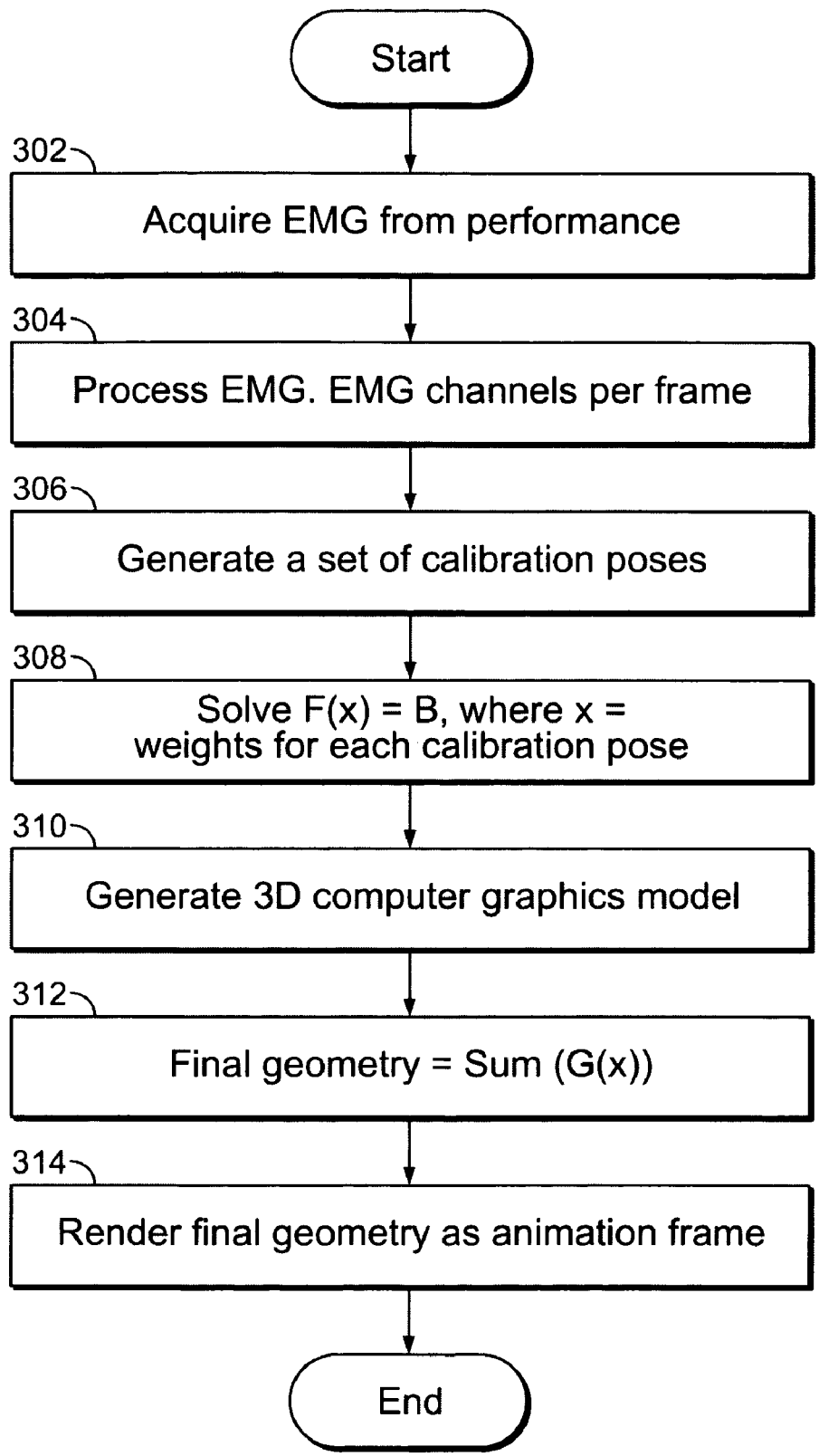
FIG. 3 is a method for producing an animation frame using electromyography (EMG) signals in accordance with an embodiment of the invention.

FIG. 3 illustrates an exemplary implementation of a facial tracking method in accordance with an embodiment of the invention. The method initially involves acquiring the EMG signal at step 302, which includes placing electrodes on specific parts of the face as discussed above. For example, the electrodes may be placed above selected facial muscle groups. Thus, when the performer makes facial expressions, the facial muscles involved create a muscle action potential in accordance with movements of the facial muscles. The acquired EMG signal is processed at step 304 to create a well-behaved signal. The EMG signal processing includes processing of the plurality of EMG channels for each frame of a facial expression. A set of calibration expressions or poses defining an n-dimensional "expression space" is then generated at 306. The calibration expressions or poses may be mathematically expressed by creating a matrix representing a matrix product of the calibration poses and the EMG channel values. To produce each calibration expression, the performer causes certain isolated muscle groups to actuate in order to calibrate the collected data. For example, the performer causes the eyebrows to move upward, and the signal from the associated EMG electrodes is measured. A calibration factor may be applied to the detected signal in order to achieve corresponding movement of the digital model. The position of the EMG electrodes may also be moved slightly in order to detect a stronger signal or to avoid cross-talk from adjacent EMG sensors. A similar process would then be repeated for each other muscle group.

The EMG signal from subsequent performances is fitted to the calibration expressions to generate weighted coefficients for each expression component at step 308. The weighed coefficients (x) are generated by solving an equation F(x)=B for x, where F is the set of calibration expressions generated at step 306, and B is the plurality of EMG channels for each frame processed at step 304. For each facial expression component, an analogous 3D computer graphics model of a face is generated at step 310. The 3D computer graphics model represents the same facial expression using a different set of parameters. For example, geometric coordinates can be used as parameters to represent the facial expression. In another example, muscle strengths can be used as parameters to represent the facial expression. When the weighted components are combined with the 3D computer graphics model at step 312, the result is a facial expression geometry matching that of the original performance. The final geometry of the facial expression is expressed as a sum of the 3D computer graphics model configured with a set of parameters and the weight components, and rendered as an animation frame at step 314.

Figure 4:
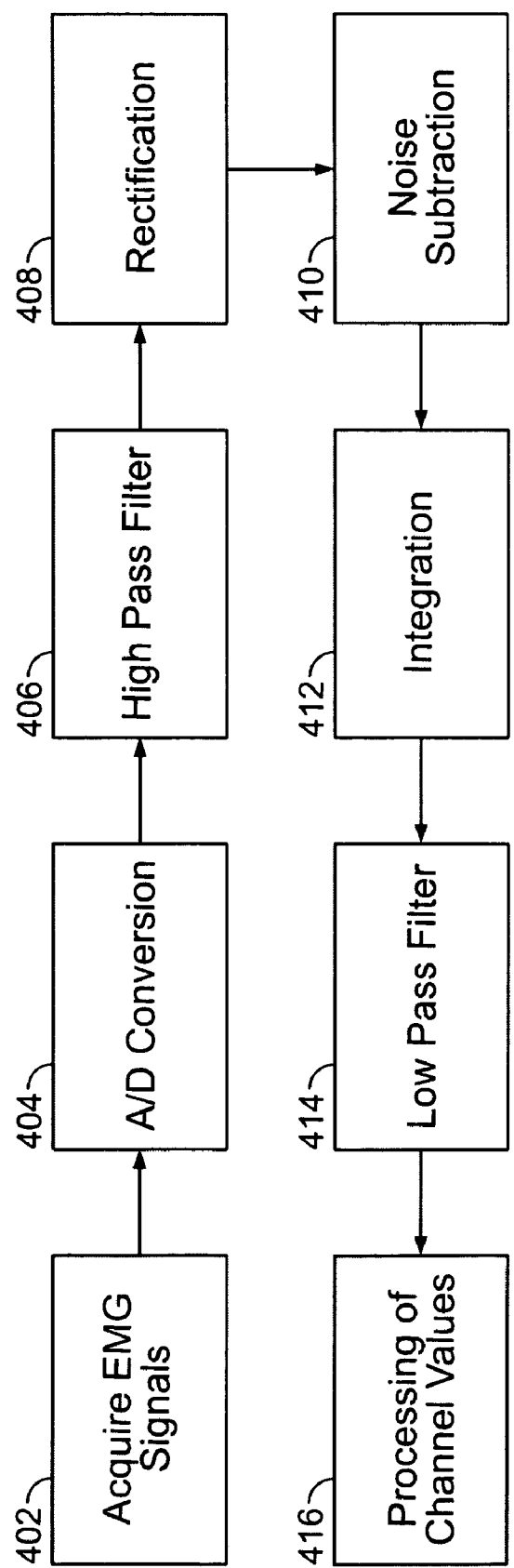
FIG. 4 is a method for processing an EMG signal.

FIG. 4 is a block diagram illustrating in greater detail an electrical circuit for processing of an EMG signal as described above in step 304. The EMG signal is acquired at 402, such as using electrodes placed on facial muscles as substantially described above. The acquired analog EMG signal is converted into a digital signal by the A/D converter 404. The high-pass filter 206 filters and the rectifier 208 rectifies the EMG signal. The noise is then subtracted from the rectified EMG signal by the noise subtraction circuit 410. The noise-reduced signal is integrated by the integrator 412, and is low-pass filtered by the low-pass filter 414. Lastly, the EMG channel values are processed by the processor 416.

Figure 5:
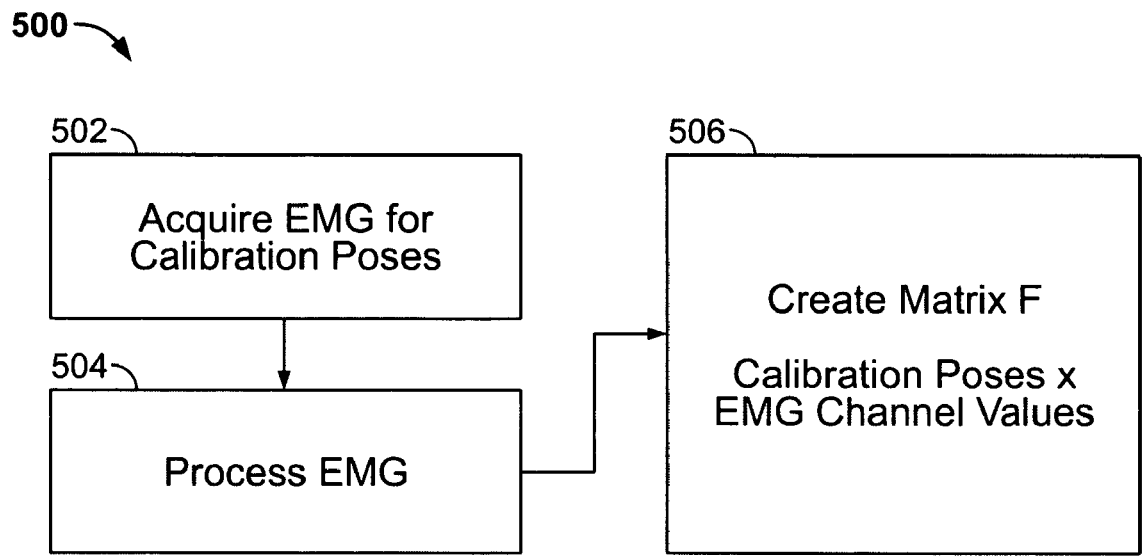
FIG. 5 is a method for processing a calibration pose.

FIG. 5 is a flow diagram illustrating in greater detail a process for generating the calibration expression as described above in step 306. Step 502 performs acquisition of EMG signals for calibration poses. The acquired EMG signals are processed at step 504. Then, step 506 generates a set of calibration expressions or poses defining an n-dimensional "expression space." As mentioned above, the calibration expressions or poses are mathematically expressed by creating a matrix representing a matrix product of the calibration poses and the EMG channel values.

Figure 8:
FIG. 8 is a photograph of a performer having facial muscular and eye potential electrodes affixed.
Figure 9:
FIG. 9 is a depiction of an animated character rendered using facial muscular and eye movement data acquired from the performer of FIG. 8.

Referring now to FIG. 8, an actual performer is shown having a plurality of EMG and EOG electrodes affixed to his face. With the electrodes affixed to the performer's face, the performer may carry out the desired performance. The electrical signals from the electrodes would be received and processed by the electrode interface 112, and communicated to the motion tracking processor 108 for storage and processing into an animation, as depicted in FIG. 9.

The bundle of electrode conductors may be bound together to facilitate ease of movement of the performer. The electrode interface 112 may multiplex the various signals onto a single conductor for communication to the motion tracking processor 108. The electrode interface 112 may be tethered to the motion tracking processor 108 by an electrical or fiberoptic conductor, or a wireless connection may be utilized to further enhance freedom of movement of the performer. Alternatively, the electrode interface 112 may include a storage device, such as a hard disk drive or flash memory module, that permits the performance data to be stored locally, and then downloaded to the motion tracking processor 108 at a later time. In an embodiment of the invention, the electrode interface 112 may be carried on the back of the performer, with the bundle of electrode conductors directed to the back of the performer's head and down along the spine to the electrode interface 112. In another alternative, the electrode interface 112 may be carried in a hat worn by the performer, which would promote free movement of the head and neck without interference by the bundle of electrode conductors. It should be appreciated that the electrodes and conductors may be integrated with a flexible mask that is form-fitted to the performer's face.

The motion tracking processor will produce a digital model of an animation character using known techniques. The digital model may be based on a plurality of digital photographs taken of the actor from various angles that are assembled together to produce a three-dimensional (3D) image file or digital model. Software tools to produce a 3D image file are well known in the art, as discussed above. For example, a 3D facial structure may be generated from a plurality of spline surfaces that each define a portion of the surface of the facial structure. The spline surfaces are formed from individual line segments that are collectively referred to as a "wire frame." The facial structure represents a sub-facie structure that lies below the skin surface. An outer surface tissue having desired texture and color will be applied to this sub-facie structure as part of a subsequent animation process to produce an animated character. It should be understood that the shape of the facial structure will control the facial expressions formed by the animated character.

Once the digital model is created, a virtual facial muscle structure is overlaid onto the digital model of the facial structure. The human facial muscle structure is well understood in the medical literature, and the position and interconnection of the individual muscles can be readily mapped onto the digital model. Muscle actuation is achieved in the digital model by compressing a selected muscle vector or group of muscle vectors to accomplish repositioning of the corresponding plurality of vertices and thereby reshape the surface of the digital model. The facial and eye motion data captured from the performer is then mapped to the respective muscle vectors of the digital model. As a result, the animated digital model will exhibit the same facial and eye movements from the captured performance. It should be appreciated that the performer's actions and expressions can be mapped onto any other kind of animated face, such as a child, animal or different looking adult face.

As noted above, the foregoing motion tracking system will enable the close coordination of facial muscle and eye motion. For example, an eye blink will be detected as a spike of the EMG data for the muscles surrounding the eyes. When the spike is detected, the animation process could insert an eye blink to correspond with the data. This would add significantly to the realism of the resulting animation. The above-described motion tracking system has advantages over traditional facial motion tracking systems because the implementations of the present invention require no camera or motion capture volume. This means that the implementation will still work even if the face to be tracked is occluded from view. Further, the implementations of the present invention automatically parameterize motion capture into muscle activity, independent of final geometry, and thus aid facial motion capture re-targeting.

While the foregoing description addressed only the capture of facial muscle movement, it should be appreciated that the same technology would permit capture of body muscle movement. The electrode pairs could be affixed to various body muscle groups in the same manner as the facial muscles described above. Likewise, a form-fitted body suit could be arranged with the EMG electrodes provided therein to improve the ease and accuracy of affixing the electrodes to the performer's body. This form of body muscle capture could further be an enhancement to conventional motion capture using optical systems, in that muscle flexure could be captured in addition to joint rotation. This would result in more lifelike animation of human movement.

It should be understood that the eye motion process described above could also be used with conventional motion capture systems using optical data to capture motion. The eye motion could then be synchronized with the optically captured body and/or facial motion is the same manner as described above. Moreover, an EMG data capture system used in conjunction with a convention optical motion capture system would provide enhanced data regarding a performance, and could be used at times where optical data is occluded due to optical interference during a performance.

Having thus described a preferred embodiment of a system and method that enables capture of facial and eye motion of a performer without the use of cameras, it should be apparent to those skilled in the art that certain advantages of the invention have been achieved. It should also be appreciated that various modifications, adaptations, and alternative embodiments thereof may be made within the scope and spirit of the present invention. The invention is further defined by the following claims.

What is claimed is:

1. A motion tracking animation system, comprising:

a plurality of pairs of electromyography (EMG) electrodes adapted to be affixed to a skin surface of a performer at plural locations corresponding to respective muscles, wherein at least one pair of EMG electrodes is aligned along an expected direction of an electrical signal corresponding to muscle movements of the performer when the electrical signal is to be read, and at least one pair of EMG electrodes is aligned along a direction perpendicular to the expected direction of the electrical signal when the electrical signal is to be excluded;

a processor operatively coupled to said plurality of pairs of EMG electrodes, said processor including programming instructions to perform the functions of:

acquiring EMG data from said plurality of pairs of EMG electrodes, said EMG data comprising electrical signals corresponding to muscle movements of the performer during a performance;

processing the EMG data to provide a digital model of the muscle movements, wherein the digital model further comprises a virtual facial muscle structure; and mapping the digital model onto an animated character, the animated character will exhibit the same muscle movements as the performer when corresponding muscle vectors within the virtual facial muscle structure are actuated in response to the acquired EMG data; and a plurality of pairs of electrooculogram (EOG) electrodes adapted to be affixed to said skin surface of the performer at locations adjacent to the performer's eyes, said processor operatively coupled to said plurality of pairs of EOG electrodes and including programming instructions to perform the functions of:

acquiring EOG data from said plurality of pairs of EOG electrodes, said EOG data comprising electrical signals corresponding to orientations of the performer's eyes during a performance;

processing the EOG data by determining a magnitude and a polarity of a dipole electric field associated with the performer's eyes in order to reconstruct the orientations of the eyes; and mapping the processed EOG data onto the animated character, wherein the animated character will exhibit the same eye orientations as the performer when corresponding muscle vectors within the virtual facial muscle structure are actuated in response to the acquired EOG data.

2. The system of claim 1, wherein said processing function further includes generating a set of calibration poses based in part on the processed EMG data.

3. The system of claim 1, wherein said acquiring EMG data function further includes rectifying and/or filtering the electrical signals.

4. The system of claim 1, wherein said processor further comprises a computer graphics animation processor.

5. The system of claim 1, further comprising an electrode interface coupled to said plurality of EMG electrodes, said electrode interface providing a composite signal to said processor.

6. The system of claim 5, wherein said electrode interface is adapted to be carried on a body of the performer.

7. The system of claim 5, wherein said electrode interface has a wireless connection to said processor.

8. A method of animating using motion tracking, comprising:

affixing a plurality of pairs of electromyography (EMG) electrodes to a skin surface of a performer at plural locations corresponding to respective muscles, wherein at least one pair of EMG electrodes is aligned along an expected direction of an electrical signal corresponding to muscle movements of the performer when the electrical signal is to be read, and at least one pair of EMG electrodes is aligned along a direction perpendicular to the expected direction of the electrical signal when the electrical signal is to be excluded;

acquiring EMG data from said plurality of pairs of EMG electrodes, said EMG data comprising electrical signals corresponding to muscle movements of the performer during a performance;

processing the EMG data to provide a digital model of the muscle movements, wherein the digital model further comprises a virtual facial muscle structure;

mapping the digital model onto an animated character, wherein the animated character will exhibit the same muscle movements as the performer when corresponding muscle vectors within the virtual facial muscle structure are actuated in response to the acquired EMG data;

affixing a plurality of pairs of electoculogram (EOG) electrodes to said skin surface of the performer at locations adjacent to the performer's eyes; and acquiring EOG data from said plurality of pairs of EOG electrodes, said EOG data comprising electrical signals corresponding to orientations of the performer's eyes during a performance, processing the EOG data by determining a magnitude and a polarity of a dipole electric field associated with the performer's eyes in order to reconstruct the orientations of the eyes, and mapping the processed EOG data onto the animated character, wherein the animated character will exhibit the same eye orientations as the performer when corresponding muscle vectors within the virtual facial muscle structure are actuated in response to the acquired EMG data.

9. The method of claim 8, wherein said processing step further includes generating a set of calibration poses based in part on the processed EMG data.

10. The method of claim 8, wherein said acquiring EMG data step further includes rectifying and/or filtering the electrical signals.

11. The method of claim 8, further comprising carrying an electrode interface operatively coupled to said plurality of EMG electrodes on a body of the performer.

* * * * *